US010303849B2

(12) United States Patent
Cachovan et al.

(10) Patent No.: US 10,303,849 B2
(45) Date of Patent: May 28, 2019

(54) ONE GATE RECONSTRUCTION (71) Applicant: SIEMENS MEDICAL SOLUTIONS USA, INC., Malvern, PA (US)

(72) Inventors: Michal Cachovan, Baiersdorf (DE); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 264 days.

(21) Appl. No.: 15/314,481

(22) PCT Filed: Jun. 12, 2015

(86) PCT No.: PCT/EP2015/063205
§ 371 (c)(1),
(2) Date: Nov. 28, 2016

(87) PCT Pub. No.: WO2015/189407
PCT Pub. Date: Dec. 17, 2015

(65) Prior Publication Data
US 2017/0193159 A1    Jul. 6, 2017

Related U.S. Application Data (60) Provisional application No. 62/011,738, filed on Jun. 13, 2014.

(51) Int. Cl.
*A61B 6/00* (2006.01)
*G06K 9/00* (2006.01)
(Continued)

(52) U.S. Cl.
CPC ............ *G06F 19/321* (2013.01); *A61B 5/055* (2013.01); *A61B 5/7292* (2013.01); *A61B 6/032* (2013.01); *A61B 6/037* (2013.01); *A61B 6/4417* (2013.01); *A61B 6/5205* (2013.01); *A61B 6/5264* (2013.01); *G16H 50/50* (2018.01)

(58) Field of Classification Search
USPC ........ 382/100, 103, 106–107, 128–134, 155, 382/162, 168, 173, 181, 199, 219, 232, 382/254, 274, 276, 286–291, 305, 294; 378/4, 21, 108; 250/363.03
See application file for complete search history.

(56) References Cited

U.S. PATENT DOCUMENTS

5,228,070 A * 7/1993 Mattson ................ A61B 6/032
378/108
7,382,852 B2 * 6/2008 Edic ....................... A61B 6/032
378/4
(Continued)

*Primary Examiner* — Seyed H Azarian (57) ABSTRACT

A set of set of first modality data is received including at least one view comprising a plurality of gates. The set of first modality data is received from a first imaging modality of an imaging system. A set of second modality data is received from a second imaging modality of the imaging system. A motion corrected model of the set of first modality data is generated by forward projecting the set of first modality data including a motion estimate. An update factor for each of the plurality of views is generated by comparing at least one of the plurality of gates to the motion corrected model. The motion corrected model is updated by the update factor to generate a motion corrected image.

19 Claims, 10 Drawing Sheets

(51) Int. Cl.
    *G06F 19/00*     (2018.01)
    *A61B 6/03*     (2006.01)
    *A61B 5/055*     (2006.01)
    *A61B 5/00*     (2006.01)
    *G16H 50/50*     (2018.01)

(56) References Cited

U.S. PATENT DOCUMENTS

| | | | |
|---|---|---|---|
| 2012/0051664 A1* | 3/2012 | Gopalakrishnan | G06T 11/005 |
| | | | 382/294 |
| 2012/0305780 A1* | 12/2012 | Thiruvenkadam | A61B 6/037 |
| | | | 250/363.03 |
| 2015/0117733 A1* | 4/2015 | Manjeshwar | G06T 11/005 |
| | | | 382/131 |

* cited by examiner

ONE GATE RECONSTRUCTION

CROSS-REFERENCE TO RELATED APPLICATIONS

This application claims priority under 35 U.S.C. § 119(e) to U.S. Provisional Application Ser. No. 62/011,738 filed Jun. 13, 2014, U.S. Provisional Application Ser. No. 62/011,608 filed Jun. 13, 2014, and U.S. Provisional Application Ser. No. 62/016,679 filed Jun. 25, 2014, each of which is hereby incorporated by reference herein in their entireties.

FIELD

Aspects of the present disclosure relate in general to processing data for medical imaging, and more particularly to techniques for one gate reconstruction in medical image processing and generation.

BACKGROUND

Multi-modality imaging systems perform diagnostic scans using multiple modalities, such as, for example, magnetic resonance (MR/MRI), computed tomography (CT), positron emission tomography (PET), and/or single photon emission computed tomography (SPECT). Multiple modalities are combined to provide complimentary and/or overlapping data sets. During operation, image quality of one or more imaging modalities, such as a SPECT modality, can be affected by motion during imaging, for example, respiratory motion. When using a SPECT modality, imaging artifacts may be generated during image acquisition due to motion of the patient. In multi-modality systems, the SPECT modality requires a relatively long duration data acquisition period, on the order of several minutes (e.g., about 2 to 30 minutes per image) for a typical clinically sufficient image. Typically, a large number of SPECT data acquisitions (e.g., frames) are acquired at many different time points during this period. Consequently, patient movement is a qualitative and quantitative limiting factor in SPECT scanning.

Common current practice is to reacquire data for a patient who moves during acquisition. In current SPECT environments, list mode data (e.g., data wherein each event, or projection, is listed sequentially, parameter by parameter) is not available. Current systems acquire projections in a step and shoot fashion and cover only a limited number of angles. A projection image is generated by a sum of all detected events (e.g., projections) over a defined dwell time and incorporates gamma detections which have undergone various physical and biological phenomena, including patient movement. Motion is estimated using a global correction which averages the motion present over the whole acquisition duration and neglects any motion that happens between the different acquired views. Severe motion artifacts are generated due to the averaging.

Data sets may be gated in an attempt to reduce motion impact on the data set. Gating results in lower statistics in each gate for nuclear (e.g., SPECT, PET) modalities, producing fewer projections per gate. The separate gates are noisier than summed datasets, as each of the gates includes a set of independent measurements each distorted by a different motion matrix. The reconstruction of the image and the noise in each gate have a higher correlation than summed reconstructions.

SUMMARY

In various embodiments, a method of processing data for medical imaging is disclosed. The method includes a step of providing a set of first modality data including at least one view. The at least one view comprises a plurality of gates. A set of second modality data is provided. An image estimate is generated for the at least on view from the set of first modality data. A motion corrected data model of the at least one view is generated by forward projecting the at least one view using a motion estimate. An image update factor is generated for the at least one of view by comparing at least one of the plurality of gates to the motion corrected data model. The image estimate is updated by the image update factor.

In various embodiments, a non-transitory computer readable medium storing computer executable instructions is disclosed. The executable instructions cause a computer to execute a step of generating a set of first modality data including at least one view. The set of first modality data is generated by a first modality of an imaging system. The executable instructions further cause the computer to execute the step of generating a set of second modality data including the at least one view. The set of second modality data is generated by a second modality of the imaging system. The executable instructions further cause the computer to execute the steps of generating an image estimate of each of the at least one view, generating a motion corrected data model of the at least one view by forward projecting the image estimate using a motion estimate, calculating an image update factor by comparing at least one of the plurality of gates to the motion corrected data model, and updating the image estimate by the image update factor.

In various embodiments, a system is disclosed. The system comprises a first imaging modality, a second imaging modality, and a computer in data communication with the first imaging modality and the second imaging modality. The computer is configured to process data for medical imaging by receiving a set of first modality data including at least one view from the first imaging modality and receiving a set of second modality data including the at least one view from the second imaging modality. The computer generates an image estimate of each of at least one view and generates a motion corrected data model of the at least one view by forward projecting the image estimate using a motion estimate. The computer further calculates an image update factor by comparing at least one of the plurality of gates to the motion corrected data model and updates the image estimate by the image update factor.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Various embodiments of the present disclosure address the foregoing challenges associated with qualitative and quantitative accuracy of medical imaging, for example, by utilizing one-gate reconstruction method that generates an intra-reconstruction motion correction for gated data.

Figure 1:
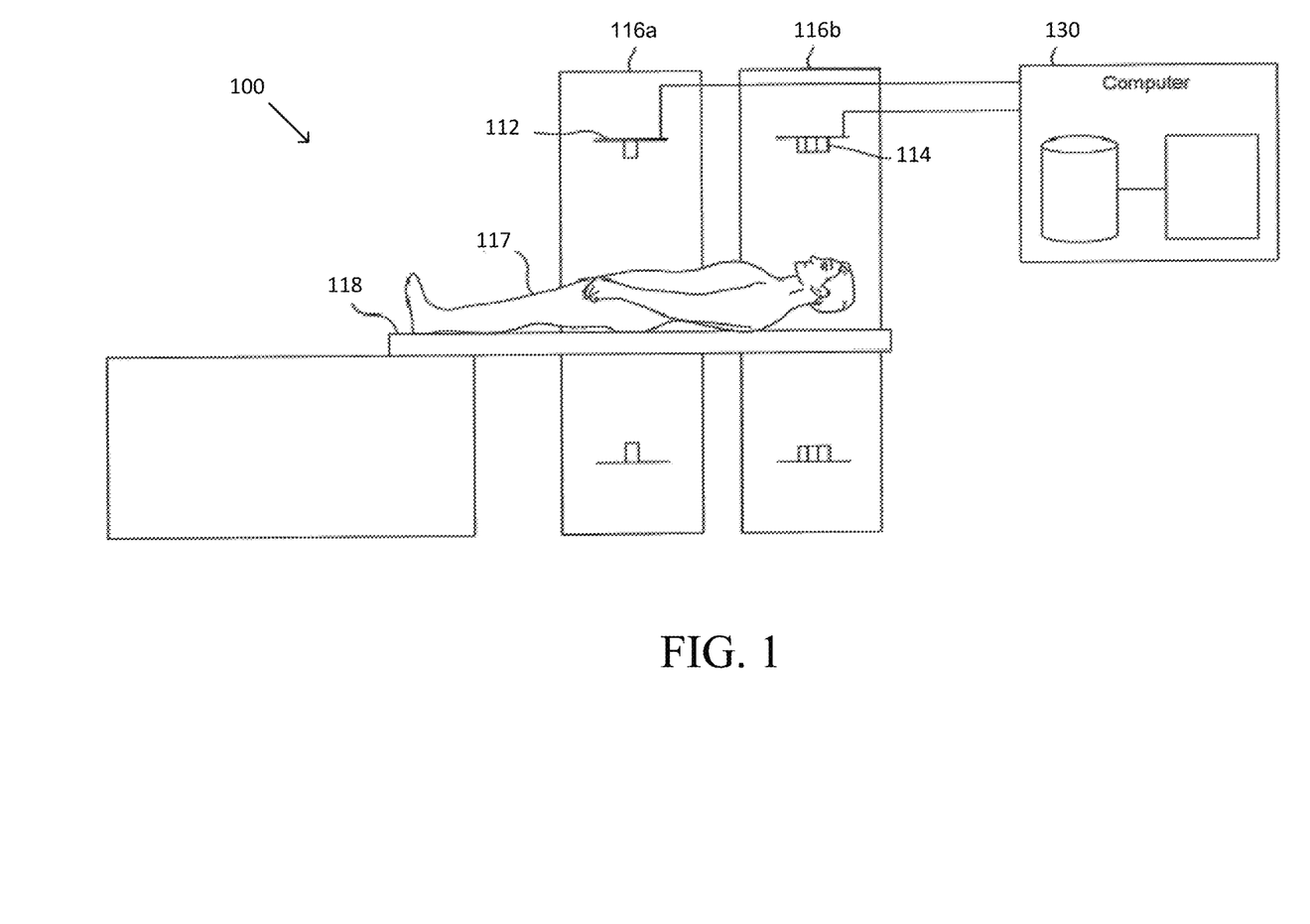
FIG. 1 illustrates one embodiment of a multi-modality imaging apparatus.

FIG. 1 shows one example of a multi-modality imaging apparatus 100. The multi-modality imaging apparatus 100 may be configured for two or more imaging modalities, such as, for example, combined PET/MR, PET/CT, SPECT/MR, SPECT/CT, and/or any other suitable combined diagnostic imaging modalities. The multi-modality imaging apparatus 100 includes a scanner for at least a first imaging modality 112 provided in a first gantry 116a and a scanner for a second imaging modality 114 provided in a second gantry 116b. In various embodiments, SPECT and CT are described as examples of first and second imaging modalities respectively that may be used in various embodiments, but it will be recognized that SPECT and CT are non-limiting examples. A patient 117 lies on a movable patient bed 118 that may be movable between the gantries. Alternatively, the two imaging modalities 112 and 114 may be combined together in a single gantry.

Scan data from at least the first and second imaging modalities 112, 114 are stored at one or more computer databases 140 and processed by one or more computer processors 150 of a computer 130. Scan data from the first and second imaging modalities may be stored in the same database 140 or in separate databases. The graphical depiction of computer 130 in FIG. 1 is provided by way of illustration only, and computer 130 may include one or more separate computing devices. In some embodiments, the computer 130 is configured to generate a partial and/or a whole body reconstructed image from a first modality data set and a second modality data set. The first and second modality data sets can be provided by the first imaging modality 112 and the second imaging modality 114 and/or may be provided as a separate data set, such as, for example, from memory coupled to the computer 130.

In some embodiments, the first and second imaging modalities 112, 114 are SPECT and CT modalities, respectively. For example, a patient can be scanned with the first imaging modality 112 and the second imaging modality 114 to yield SPECT acquisition and physiological waveform data and segmented CT data, respectively. The scans may be performed sequentially, with a CT scan following a SPECT scan, and/or simultaneously. In another embodiment, the first imaging modality 112 is CT and the second imaging modality 114 is SPECT. In some embodiments, the second imaging modality 114 is a nuclear imaging modality.

In some embodiments, the data acquisition time of one of the imaging modalities, such as, for example, the first imaging modality 112 is greater than the data acquisition time of the other imaging modality, for example, the second imaging modality 114. In some embodiments, the first imaging modality 112 is a SPECT imaging modality and the second imaging modality 114 is a CT imaging modality. The SPECT imaging modality is configured to acquire a plurality of views (or angles). Each angle comprises a plurality of projections detected by the SPECT imaging modality over a predetermined time period. In some embodiments, each view in the SPECT image data may be acquired over a relatively long period, such as, for example, 30 minutes. Because of the length of each acquisition of the SPECT imaging modality, patient motion limits the qualitative and quantitative accuracy of each obtained view. The CT imaging modality is configured to acquire a similar plurality of views as the SPECT imaging modality. The CT imaging modality obtains each view over a shorter predetermined time period, such as, for example, two seconds. The shorter time period of the CT imaging modality avoids the introduction of motion errors and allows for motion correction of the SPECT imaging modality.

In some embodiments, gating is performed based on an acquired physiological signal to determine gate locations (in time) and a gate width (in time duration) for one or more gates. Any gating algorithm known in the art can be used for this purpose. Gate width, i.e., the time duration of a gate, depends on the imaging modality. The widths (time durations) of respective gates in a cycle may be constant or may vary, e.g., depending on the gating algorithm that is used and the constraints of the imaging modality.

Although combined SPECT and CT system are discussed herein, it will be recognize that the disclosed systems and methods are applicable to any combined modalities, such as, for example, MR/PET, CT/PET, MR/SPECT, and/or CT/SPECT.

In some embodiments, a one-gate reconstruction method is applied to one or more sets of gated imaging data acquired by the imaging apparatus 100. The gated imaging data includes one or more views each containing a plurality of gates. Each of the gates contains a subset of the view data. The gates may be evenly spaced and/or unevenly spaced. The one-gate reconstruction method corrects for inter-view and inter-gate motion and enables corrections on a view-by-view basis. In some embodiments, data from multiple gates in each view are merged into a single reconstructed image using a one-gate reconstruction method. For example, in some embodiments, each gate of a set of first modality data is incorporated as a subset of data set provided to an intra-reconstruction motion correction method. As another example, in some embodiments, an optimized update factor is generated using the gates of each view. In some embodiments, the one-gate reconstruction method is an iterative reconstruction method that uses an intra-reconstruction motion correction method to correct for inter-view and inter-gate motion errors.

Figure 2:
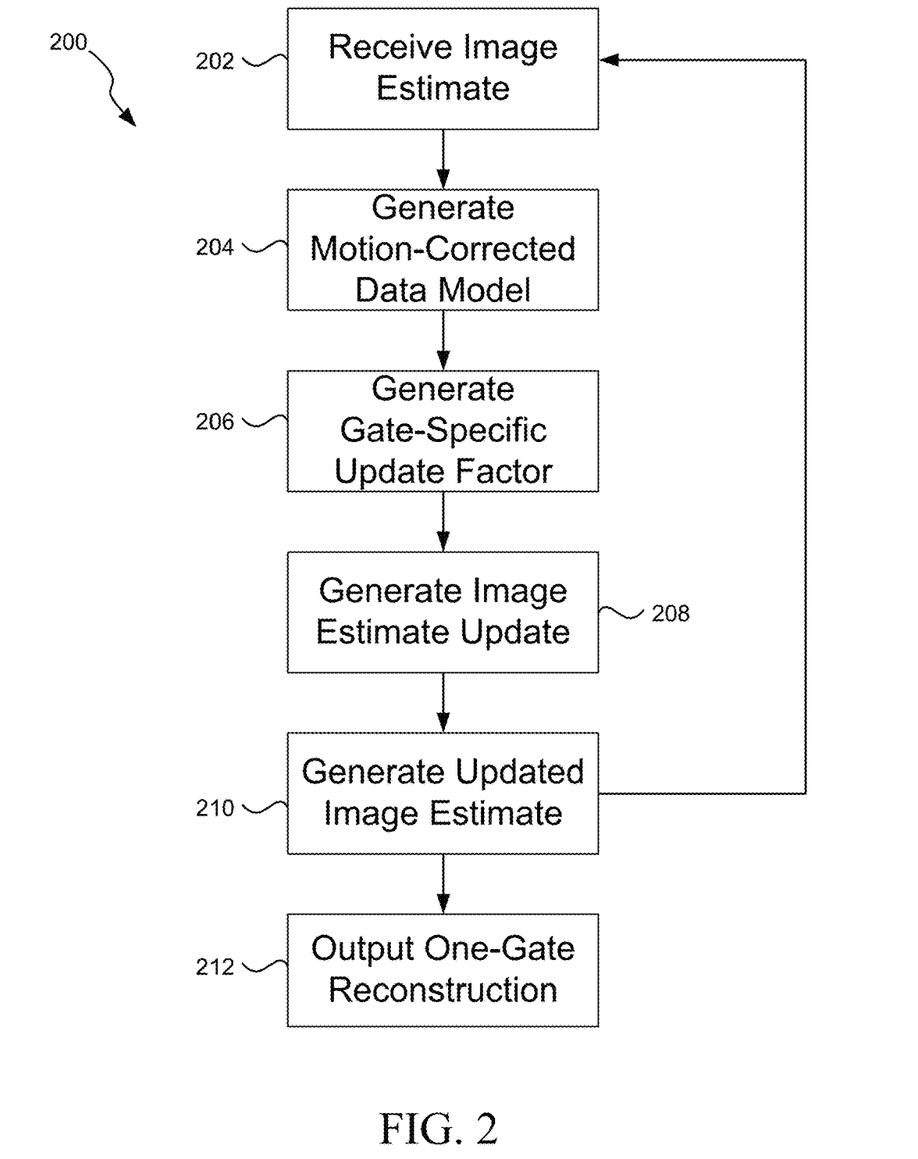
FIG. 2 illustrates one embodiment of a one-gate reconstruction method that utilizes each gate as an independent input to the reconstruction.

FIG. 2 illustrates one embodiment of a one-gate reconstruction method 200. The one-gate reconstruction method 200 is applied to each view in a set of first modality data, such as, for example, a set of first modality data obtained by the first imaging modality 112 of the imaging apparatus 100. In some embodiments, the first modality is a SPECT modality, although it will be appreciated that the one gate reconstruction method 200 can be applied to any suitable gated modality data set. An image estimate is generated 202 for a view in a set of first modality data. The image estimate may be generated by any suitable method, such as, for example, a non-motion corrected method and/or a motion-corrected method. In some embodiments, the image estimate is received from a remote system, such as a memory device coupled to the computer 130.

Figure 3:
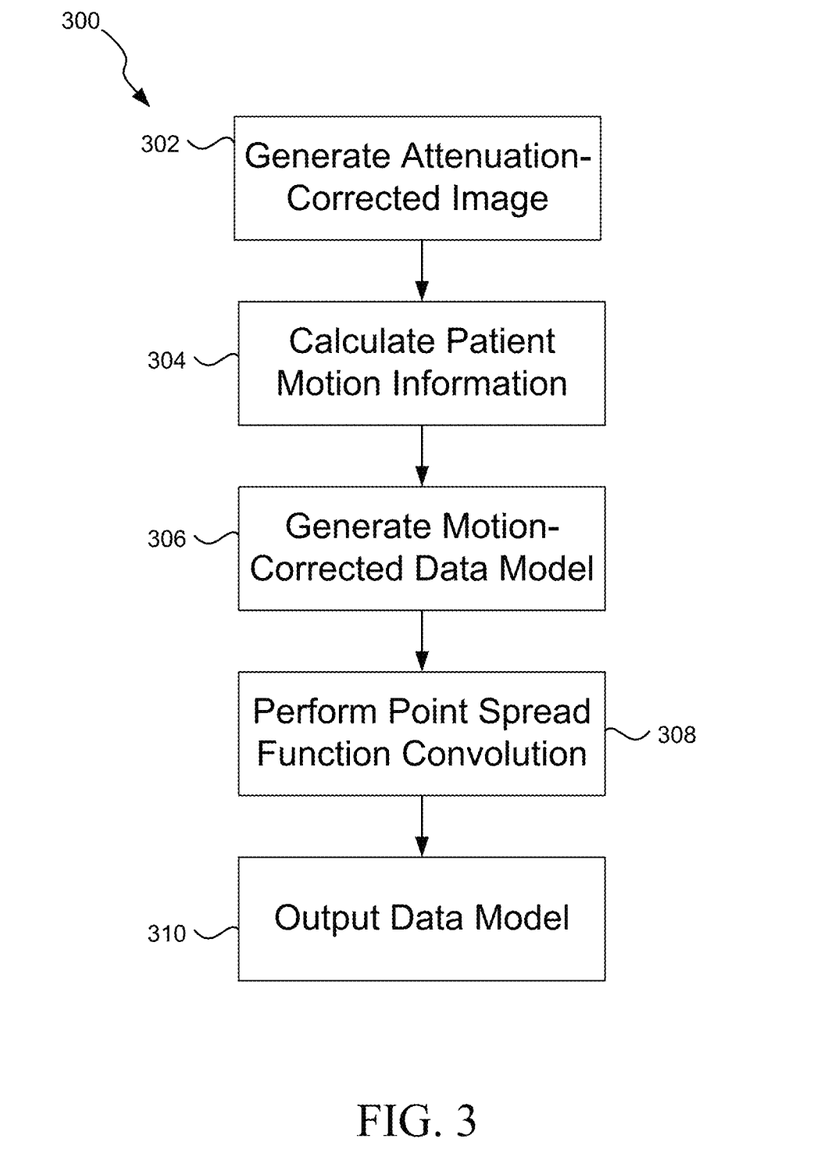
FIG. 3 illustrates one embodiment of a method for motion corrected forward projection.

At step 204, a motion information for the image estimate is generated. In some embodiments, the motion information is generated by a forward projection method. The forward projection method can include an intra-reconstruction motion correction method. FIG. 3 illustrates one embodiment of an intra-reconstruction motion correction method 300 that may be applied as part of the one-gate reconstruction method 200. An attenuation-corrected model is generated 302 by combining angle-dependent (or view-dependent) attenuation maps and the previously generated view-specific image estimate. In some embodiments, each of the angle-specific attenuation maps are pre-computed and provided to a system implementing the intra-reconstruction motion correction method 300, such as, for example, the computer 130 of imaging apparatus 100. In other embodiments, the attenuation maps are calculated as part of the method 300. One or more modeling processes, such as, for example, acquisition information correction, gantry deflection correction, and/or any other required system modeling processes may be included in the generation 302 of the attenuation-corrected model. The attenuation maps and the image estimate can be combined by, for example, a tensor function to generate an attenuation-corrected model. In some embodiments, generation 302 of the attenuation corrected model is performed simultaneously with other portions of the intra-reconstruction motion correction method 300.

Next, patient motion information is calculated 304 for the current view of the first modality data. The patient motion information may be calculated 304 by, for example, a patient motion assessment tool. The patient motion assessment tool is configured to perform motion estimation in the image space and/or the projection space. The patient motion assessment tool utilizes a set of second modality data (such as, for example, CT and/or MR data) which is projected into the projection data space of the set of first modality data. The projected second modality data is registered (e.g., aligned) with the set of first modality data on a view-to-view basis. In some embodiments, the set of second modality data is segmented to separate significant tissue from non-significant tissue. A rigid and/or a non-rigid registration technique may be used to align the set of first modality data with the set of second modality data. The set of second modality data may be obtained, for example, by the second imaging modality 114 of the imaging apparatus 100 and/or may be provided by a remote system. The second imaging modality 114 may comprise any suitable imaging modality, such as, for example, a morphological modality (e.g., CT, MR, etc.) and/or a nuclear modality (e.g., PET). The patient motion assessment tool can comprise any suitable patient motion assessment tools, such as, for example, using tracking devices, registration techniques, and/or data tracking techniques. In some embodiments, the coordinate system of the motion estimation is rotated 314 to match the coordinate system of the attenuation-corrected model.

The patient motion information calculation 304 generates a motion field and/or a motion matrix. A motion-corrected data model of the first modality view data is generated 306 by a forward projection. The attenuation-corrected projection incorporates the motion information (e.g., motion field and/or motion matrix) provided by the patient motion estimation tool to generate 306 the motion-corrected data model. In some embodiments, a point spread function convolution is performed 308 to model a depth dependent detector response of the first modality. In some embodiments, the point spread function convolution includes a Fast Fourier Transform (FFT) of the motion-corrected model. The FFT is combined with a Point Spread Function (PST) in the FFT domain through a tensor product. The tensor products of each model for each view in the first data set are summed and an Inverse Fast Fourier Transform (IFFT) is performed to convert back into the image space. PCT International Application No. PCT/EP2015/063190, entitled "Intra Reconstruction Motion Correction," and filed concurrently with the present application, is incorporated by reference herein in its entirety. The intra-reconstruction motion-corrected method 300 outputs a motion-corrected data model to the one-gate reconstruction method 200.

In some embodiments, a pre-processing step (not shown) may generate a motion estimation for each of the gates in the set of first modality data. The motion estimates for each of the gates may be used during the intra-reconstruction motion corrected method 300 to improve the motion-corrected data model. For example, in some embodiments, the motion estimate may be refined iteratively by the intra-reconstruction motion corrected method 300 to generate an iterative motion-corrected data model for use in the one-gate reconstruction method 200.

Referring back to FIG. 2, in step 206, the motion-corrected data model generated by the intra-reconstruction motion correction method 300 is compared to a set of gate data to generate a projection update factor. The update factor is generated by comparing a projection of the current gate data and the motion-corrected data model to generate a difference image. The difference image may be generated by subtracting the pixel (or projection) values of the current gate data from the motion-corrected data model.

The difference image is dependent on the merit function and/or reconstruction used to motion-correct the set of first modality data. For example, in embodiments comprising the intra-reconstruction motion correction method 300, the difference image is an array of data generated by a dividing each of the pixels in the first modality data model generated by the intra-reconstruction motion correction method 300 and each of the pixels in the gate data. In embodiments including a computer-graphics (CG) reconstruction having a Chi squared merit function, for example, the difference image is calculated as the difference between each of the pixels in the CG reconstruction and the gate data squared and normalized (e.g., multiplied by a normalization factor). The computation of the update factor is performed in the projection space on a pixel-by-pixel basis.

In step 208, the projection update factor is back projected into the image space to generate an image update factor. The back projection may be performed by any suitable method, such as, for example, a reverse of the intra-reconstruction motion correction method 300 illustrated in FIG. 3. In step 210, the first modality image estimate is updated by the image update factor to generate an updated image estimate. In some embodiments, the updated image estimate is generated by multiplying the first modality image estimate by the backward projected updated factor on a voxel-by-voxel basis. In some embodiments, the product of the first modality image estimate and the backward projected update factor is divided by a normalization factor. The step 210 produces a matrix of data corresponding to a plurality of voxels of the updated image estimate in the image space.

In some embodiments, the one-gate reconstruction method 200 is iteratively repeated for each gate in the view-data of the first data set. For example, after an updated image estimate is generated at step 210, the updated image estimate can be provided as a new input to the one-gate reconstruction method 200. The method 200 is applied iteratively for each subsequent gate of in the current view of the set of first modality data. The iterative method 200 continues until each gate has been considered. After all gates have been processed, a step 212 outputs a one-gate reconstructed image.

Figure 4:
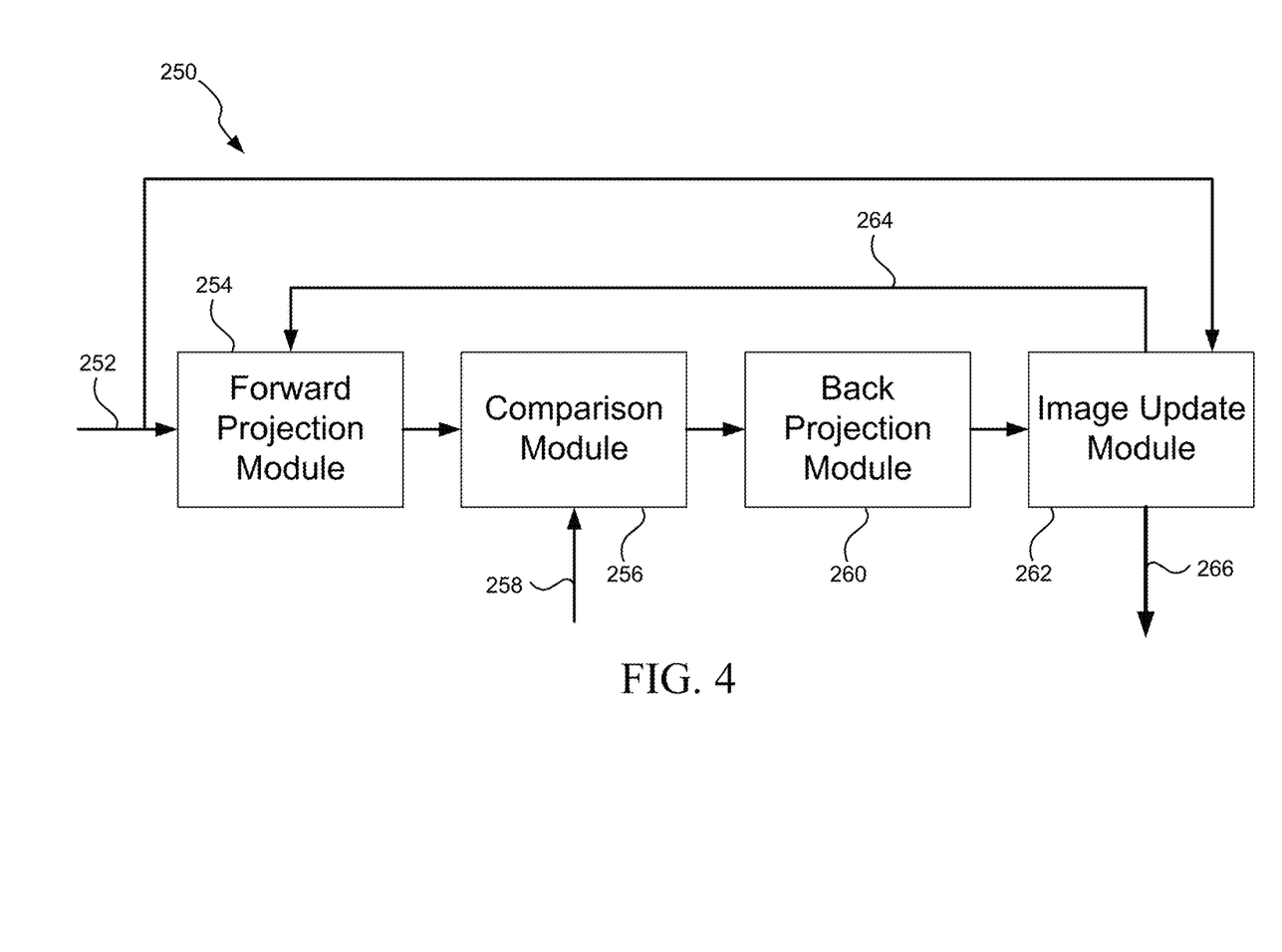
FIG. 4 illustrates one embodiment of a system configured to implement the one-gate reconstruction method illustrated in FIG. 2.

FIG. 4 illustrates one embodiment of a system 250 configured to implement the one-gate reconstruction method 200 illustrated in FIG. 2. The system 250 includes an intra-reconstruction motion correction module 254 configured to receive an image estimate 252 of a view in a set of gated first modality data. The intra-reconstruction motion correction module 254 generates a motion-corrected data model of the image estimate 252 and provides the motion-corrected data model to a comparison module 256. The comparison module 256 receives gate data 258 corresponding to a current gate (e.g., first gate, second gate, . . . , Nth gate) of the current view. The comparison module 256 compares the gate data 258 to the motion-corrected model to generate a gate-specific update factor. The gate-specific update factor is provided to a back projection module 260. The back projection module 260 back projects the gate-specific update factor from the projection space to the image space. The back projection module 260 may utilize any suitable back projection method, such as a reverse of the forward projection method 300 illustrated in FIG. 3. The back projection module 260 generates an image update for the image estimate 252 of the current view in the set of first modality data. The image update is provided to an image updater module 262 which updates the image estimate 252. In some embodiments, the updated image 264 is provided as an input to the intra-reconstruction motion correction module 254. The system 250 is configured to update the image estimate 264 for each gate (e.g., first gate, second gate, . . . , Nth gate) in the current view of the first modality data. After updating the image estimate 264 for each gate in the current view. the image updater module 262 outputs a one-gate reconstructed image 266. The one-gate reconstructed image 266 may be displayed by any suitable display, stored in a memory module coupled to the system 250, and/or provided to a user for diagnostic and/or other medical purposes.

Figure 5:
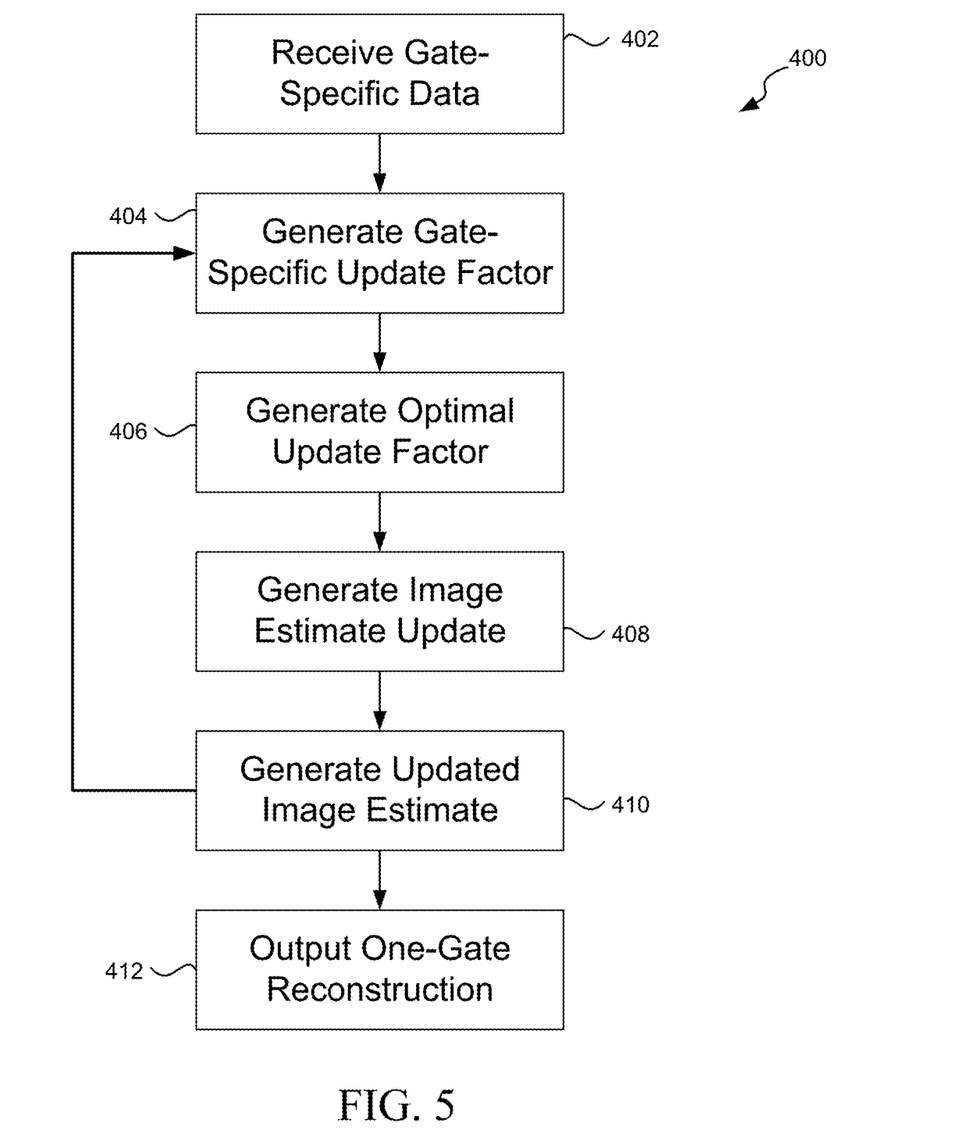
FIG. 5 illustrates one embodiment of a one-gate reconstruction method that generates an optimized update factor from the gated data.

FIG. 5 illustrates one embodiment of a one-gate reconstruction method 400 configured to generate an optimal update factor from a plurality of gates. In the illustrated embodiment, a set of gated first modality data is received 402. The gated first modality data comprises a plurality of gates. Each gate in the set of first modality data is compared 404 to a data model. The data model may be, for example, a raw (e.g., non-motion corrected) projection of a view in the set of first modality data and/or a motion-corrected projection. The comparison 404 between each of the plurality gates and the data model generates individual update factors for each gate with respect to the data model. In some embodiments, the individual update factors are generated by comparing a projection of the current gate data and the motion-corrected data model to generate a difference image. The different image may be determined by any suitable comparison, such as, for example, a merit function between the first modality data model and the gate data. Each of update factors are combined to generate 406 an optimal update factor for the data model. The individual update factors may be combined by any suitable method, such as a straight average, a weighted average, a regression analysis, and/or any other suitable method. The optimal update factor is back projected to the image space to generate 408 an image estimate update factor. The back projection may be performed according to any suitable method, such as a reverse of the intra-reconstruction motion correction method 300 illustrated in FIG. 3 and/or any other suitable back projection motion correction method.

The image estimate of current view the first modality data is updated 410 according to the back projection of the optimal update factor. In some embodiments, the updated image estimate is provided to a forward projection motion correction method, such as, for example, the intra-reconstruction motion correction method 300 disclosed in FIG. 3 to generate 412 an updated data model in the projection space. The updated data model may be provided to a user for diagnostic imaging. In some embodiments, the one-gate reconstruction method 400 is iteratively applied to further refine the data model. For example, in some embodiments, the updated data model is provided as an input to the one-gate reconstruction method 400. After a predetermined number of iterations of the one-gate reconstruction method 400 (or after an error rate is determined to be below a predetermined threshold) the updated data model is output 414 as a one-gate reconstructed image.

Figure 6:
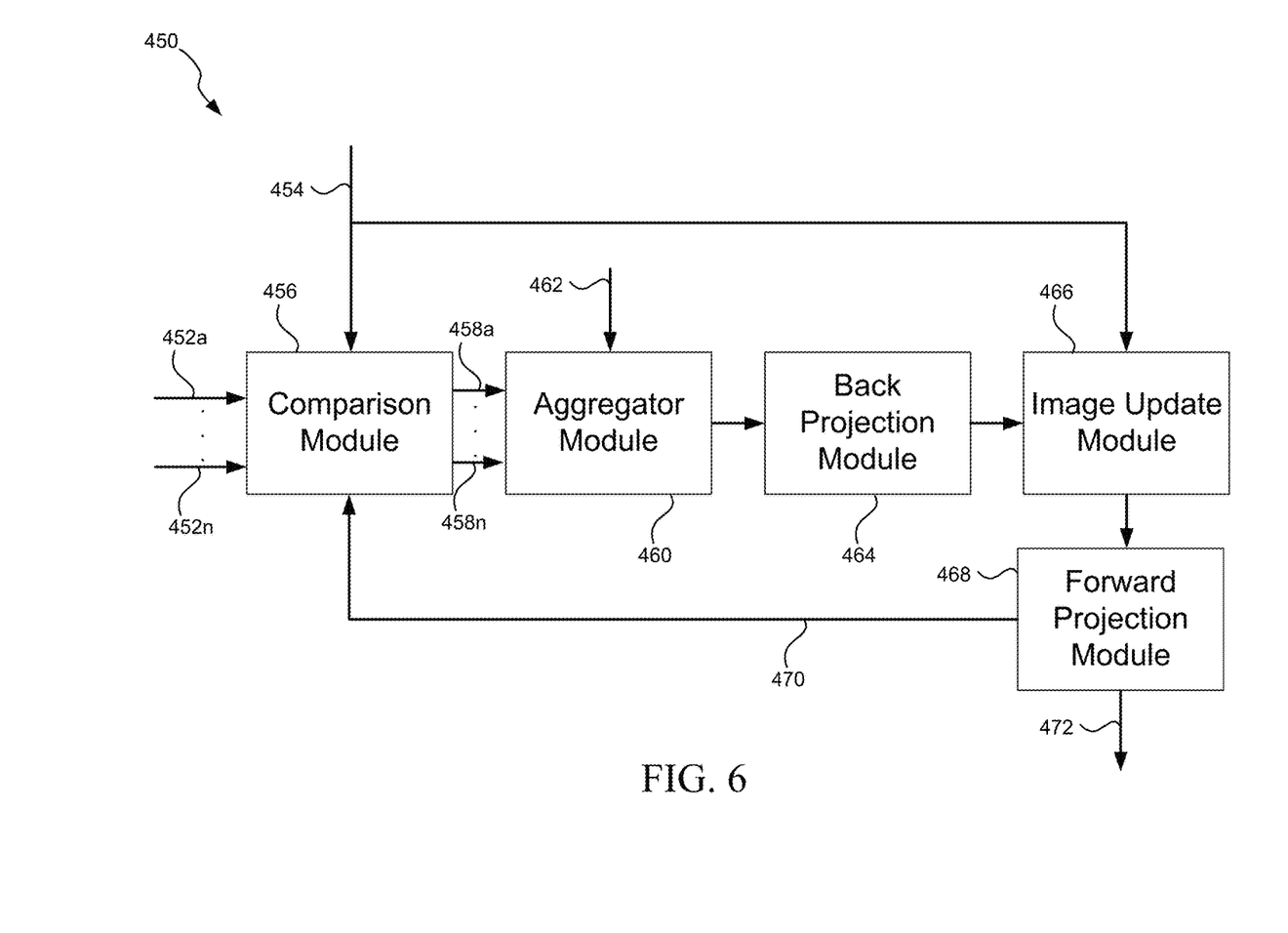
FIG. 6 illustrates one embodiment of a system configured to implement the one-gate reconstruction method illustrated in FIG. 5.

FIG. 6 illustrates one embodiment of a system 450 configured to implement the one-gate reconstruction method 400 illustrated in FIG. 5. The system 450 includes a comparison module 456 configured to receive a plurality of gate data 452a-452n for each gate (e.g., first gate, second gate, Nth gate) in a view of a set of gated first modality data. The comparison module 456 is configured to compare each gate 452a-452n in the current view to an image estimate 454. The image estimate 454 may be any suitable image model in an image space generated from the current view data. The comparison module 456 generates a gate-specific update factor 458a, 458n for each gate 452a-452n in the current view. In some embodiments the gate-specific update factors 458a, 458n are provided to a combination module 460. The combination module 460 generates an optimal update factor by aggregating each of the individual update factors 458a, 458n. The combination module 460 can aggregate the individual update factors 458a, 458n using any suitable method, such as, for example, a straight average, a weighted average, a regression analysis, and/or any other suitable method.

The optimal update factor generated by the combination module 460 is provided to a back projection module 464. The back projection module 464 back projects the optimal update factor from the projection space to the image space. The back projection module 464 may utilize any suitable back projection method, such as a reverse of the forward projection method 300 illustrated in FIG. 3. The back projection module 464 generates an optimal image update for the current view of the set of first modality data. In other embodiments, each of the individual update factors back projected by the back projection module 464 to generate a plurality of image update factors. The plurality of image update factors may be combined, for example by combination module 460, into an aggregate image update factor. In other embodiments, each of the plurality of update factors may be applied individually to the first modality image estimate.

The image update (e.g., the optimal image update, aggregate image update, and/or each of the individual image updates) is provided to an image updater module 466, which updates the image estimate 454. The updated image estimate is provided to a forward projection module 468. The forward projection module 468 generates an updated data model by forward projecting the updated image estimate into the projection space. The forward projection module 468 may utilize any suitable forward projection method, such as the forward projection method 300 illustrated in FIG. 3.

In some embodiments, the updated data model 470 generated by the forward projection module 468 is provided as an input to the comparison module 456. The comparison module iteratively compares the updated data model 470 to the plurality of gates 452a, 452n to further correct the date model/image estimate. After a predetermined number of iterations, the forward projection module 468 outputs a one-gate reconstructed image 472. The one-gate reconstructed image 266 may be displayed by any suitable display, stored in a memory module coupled to the system 250, and/or provided to any a user for diagnostic and/or other medical purposes.

Figure 7:
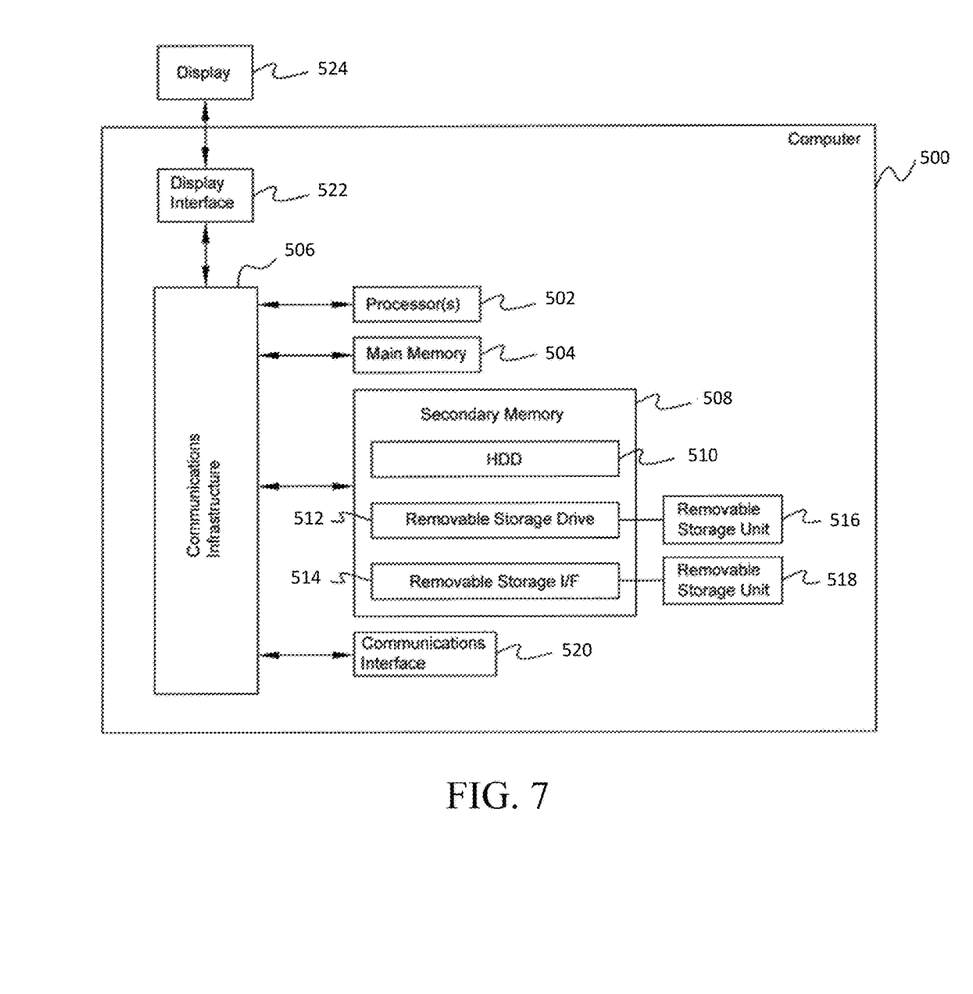
FIG. 7 is an architecture diagram of a computer system that may be used in some embodiments.

FIG. 7 is an architecture diagram of a computer system 500 that may be used in some embodiments, e.g., for implementing computer 130 shown in FIG. 1. Computer system 500 may include one or more processors 502. Each processor 502 is connected to a communication infrastructure 506 (e.g., a communications bus, cross-over bar, or network). Computer system 500 may include a display interface 522 that forwards graphics, text, and other data from the communication infrastructure 506 (or from a frame buffer, not shown) for display on the display unit 524 to a user.

Computer system 500 may also include a main memory 504, such as a random access memory (RAM), and a secondary memory 508. The main memory 504 and/or the secondary memory 508 comprise non-transitory memory. The secondary memory 508 may include, for example, a hard disk drive (HDD) 510 and/or removable storage drive 512, which may represent a floppy disk drive, a magnetic tape drive, an optical disk drive, a memory stick, or the like as is known in the art. The removable storage drive 512 reads from and/or writes to a removable storage unit 516. Removable storage unit 516 may be a floppy disk, magnetic tape, optical disk, or the like. As will be understood, the removable storage unit 516 may include a computer readable storage medium having tangibly stored therein (embodied thereon) data and/or computer software instructions, e.g., for causing the processor(s) to perform various operations.

In alternative embodiments, secondary memory 508 may include other similar devices for allowing computer programs or other instructions to be loaded into computer system 500. Secondary memory 508 may include a removable storage unit 518 and a corresponding removable storage interface 514, which may be similar to removable storage drive 512, with its own removable storage unit 516. Examples of such removable storage units include, but are not limited to, USB or flash drives, which allow software and data to be transferred from the removable storage unit 516, 518 to computer system 500.

Computer system 500 may also include a communications interface (e.g., networking interface) 520. Communications interface 520 allows software and data to be transferred between computer system 500 and external devices. Examples of communications interface 520 may include a modem, Ethernet card, wireless network card, a Personal Computer Memory Card International Association (PCMCIA) slot and card, or the like. Software and data transferred via communications interface 520 may be in the form of signals, which may be electronic, electromagnetic, optical, or the like that are capable of being received by communications interface 520. These signals may be provided to communications interface 520 via a communications path (e.g., channel), which may be implemented using wire, cable, fiber optics, a telephone line, a cellular link, a radio frequency (RF) link and other communication channels.

Figure 8A:
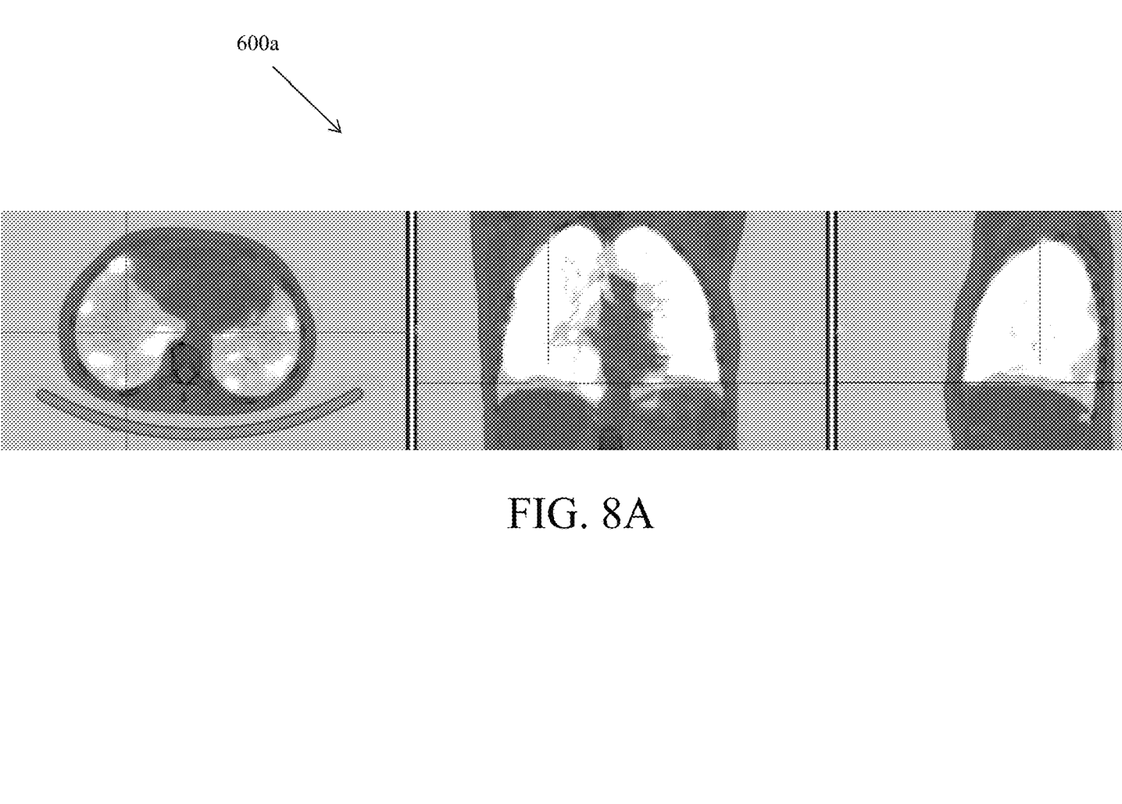
FIG. 8A illustrates one embodiment of an ungated reconstruction of a SPECT data set and a CT data set.
Figure 8B:
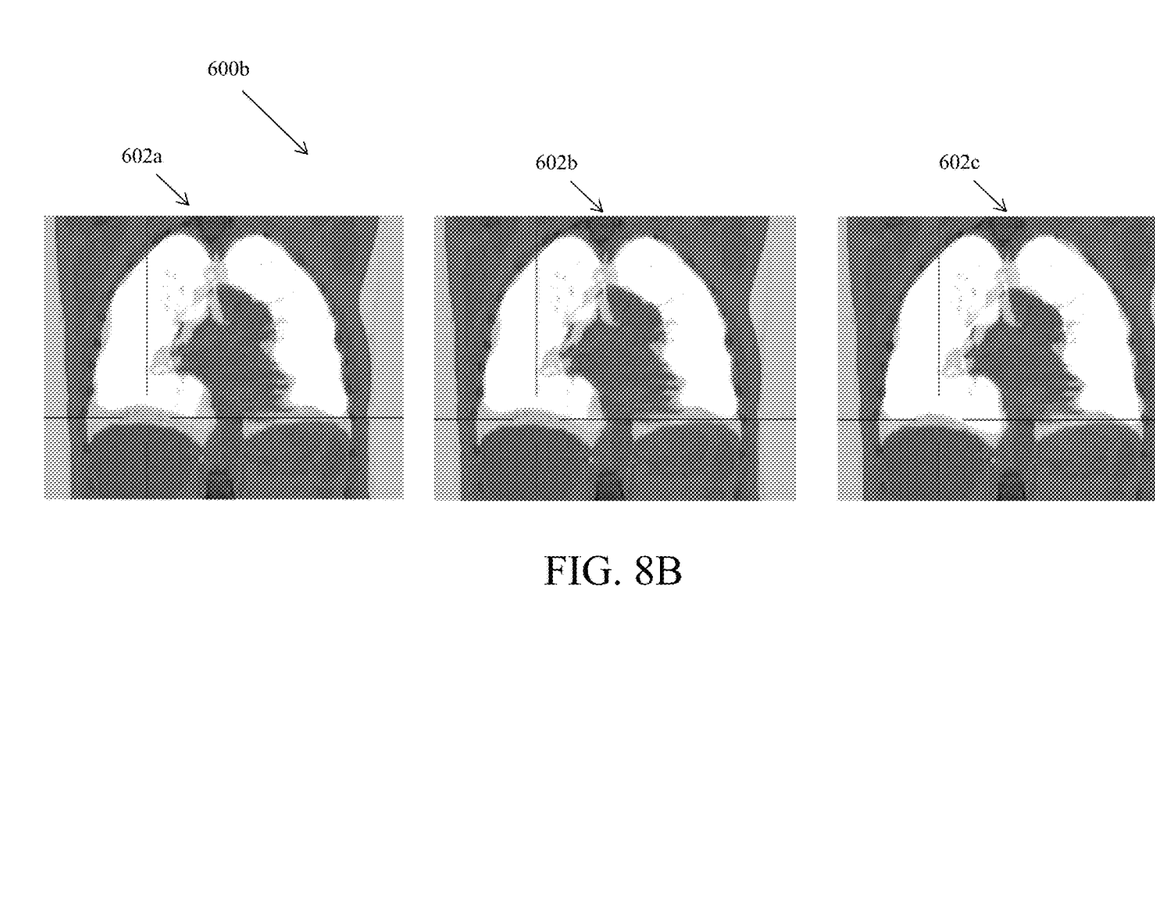
FIG. 8B illustrates one embodiment of a gated reconstruction of the SPECT data set and CT data set.
Figure 8C:
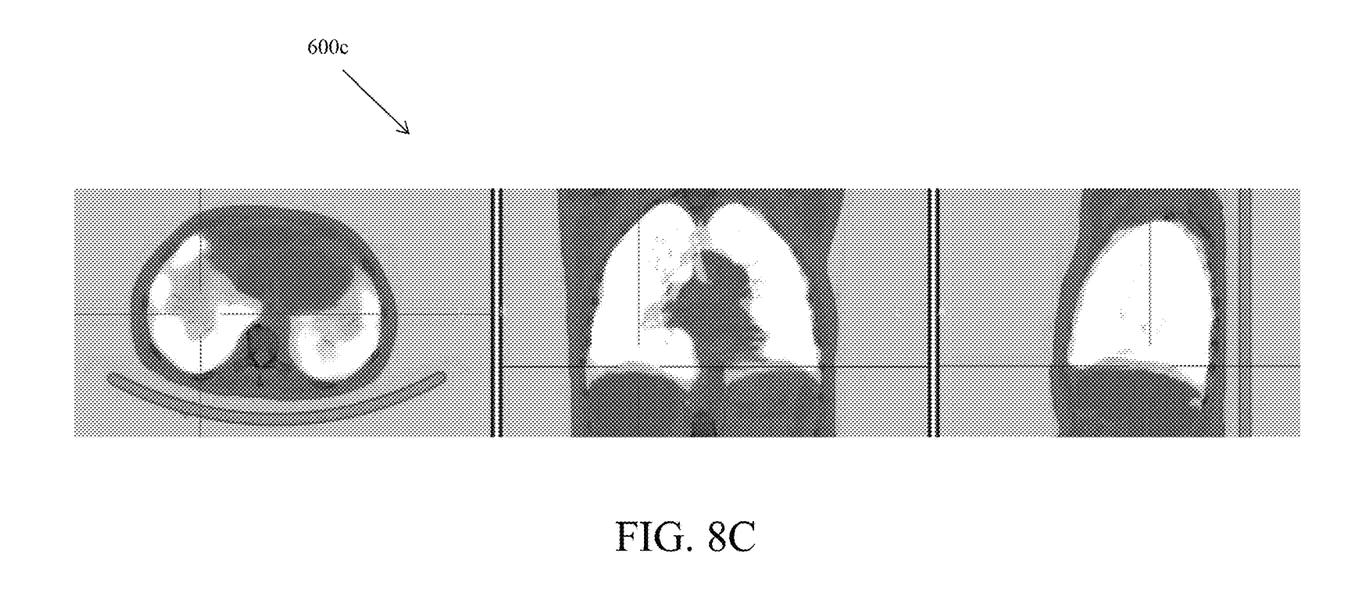
FIG. 8C illustrates one embodiment of a one-gate reconstruction of the SPECT data set and the CT data set.

FIGS. 8A-8C illustrate a one gate reconstruction of a SPECT data set and a CT data set. FIG. 8A illustrates one embodiment of an ungated reconstruction 600a. The ungated reconstruction 600a has a high signal-to-noise ratio (SNR). The position of several features, such as, for example, the diaphragm, do not match in the SPECT data and the CT data. FIG. 8A provides an imprecise quantitation of the SPECT and CT data sets. FIG. 8B illustrates one embodiment of a gated nuclear reconstruction 600b including three gates 602a-602c. Each of the gates 602a-602c illustrates a different inspiration phases. The third gate 602c has the best match of diaphragm locations between the SPECT and CT data. The gated nuclear reconstruction 600b has a high SNR, as the gating introduces additional errors into the SECT raw data. The ungated reconstruction 600a can be updated using the gates 602a-602c according to one or more of the methods disclosed herein. For example, the ungated reconstruction 600a can be updated according to the one-gate reconstruction method 200.

FIG. 8C illustrates one embodiment of a one gate reconstruction 600c of the SPECT and CT data according to the methods described herein. The ungated reconstruction 600a is combined with each of the gates 602a-602c according to, for example, the method 200 illustrated in FIG. 2. The one gate reconstruction 600c shows proper alignment between the SPECT and CT data, which provides for greater precision quantitation of the SPECT and CT data sets. The diaphragm is in an appropriate location. The one gate reconstruction 600c has an improved SNR compared to the ungated reconstruction 600a. As shown in FIG. 8C, the one gate reconstruction methods described herein provide a clearer image, providing for easier and greater identification of anomalies in an imaged patient.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of processing data for medical imaging, the method comprising:
    providing a set of first modality data including at least one view comprising a plurality of gates;
    providing a set of second modality data;
    generating an image estimate for the at least one view from the set of first modality data;
    generating a motion corrected data model of the at least one view by forward projecting the at least one view using a motion estimate;
    generating an image update factor for the at least one view by comparing at least one of the plurality of gates to the motion corrected data model, wherein generating the image update factor comprises comparing each of the plurality of gates to the motion corrected data model to generate a plurality of projection update factors, and wherein comparing each of the plurality of gates to the motion corrected data model comprises applying a merit function between the motion corrected data model and each of the plurality of gates to generate the plurality of projection update factors; and updating the image estimate by the image update factor.

2. The method of claim 1, wherein generating the image update factor further comprises:

combining the plurality of projection update factors to generate an optimal projection update factor; and back projecting the optimal projection update factor to an image space to generate an optimal image update factor.

3. The method of claim 2, wherein the plurality of projection update factors are combined by averaging of the plurality of update factors.

4. The method of claim 1, wherein generating the image update factor further comprises:

back projection each of the plurality of projection update factors into an image space to generate a plurality of image update factors; and combining the plurality of image update factors to generate an aggregate image update factor.

5. The method of claim 4, wherein the motion corrected back projection is a reverse intra-reconstruction motion corrected method.

6. The method of claim 1, wherein the steps of generating a motion corrected data model, generating an image update factor, and updating the image estimate are iteratively repeated for each of the plurality of gates in the at least one view.

7. The method of claim 1, wherein the motion corrected data model is generated by an intra-reconstruction motion correction method.

8. The method of claim 1, wherein the first modality is a SPECT modality.

9. The method of claim 8, wherein the second modality is selected from the group consisting of a CT modality and a MR modality.

10. A non-transitory computer readable medium storing computer executable instructions which cause a computer to execute the steps of:

generating a set of first modality data including at least one view, wherein the set of first modality data is generated by a first modality of an imaging system;

generating a set of second modality data including the at least one view, wherein the set of second modality data is generated by a second modality of the imaging system;

generating an image estimate of each of the at least one view;

generating a motion corrected data model of the at least one view by forward projecting the image estimate using a motion estimate;

calculating an image update factor by comparing at least one of the plurality of gates to the motion corrected data model, wherein calculating the image update factor comprises comparing each of the plurality of gates to the motion corrected data model to generate a plurality of projection update factors, and wherein calculating the image update factor further comprises combining the plurality of projection update factors to generate an optimal update factor and back projecting the optimal update factor into an image space to generate the image update factor; and updating the image estimate by the image update factor.

11. The non-transitory computer readable medium of claim 10, wherein generating the image update factor comprises:

comparing a set of first gate data to the motion corrected data model to generate a first image update factor;

updating the image estimate by the first image update factor;

comparing a set of second gate data to the motion corrected model to generate a second image updated factor; and updating the image estimate by the second update factor.

12. The non-transitory computer readable medium of claim 10, wherein the plurality of projection update factors are combined by averaging of the plurality of projection update factors.

13. The non-transitory computer readable medium of claim 10, wherein calculating the image update factor further comprises:

back projecting each of the plurality of projection update factors into an image space to generate a plurality of gated image update factors; and combining the plurality of gated image update factors to generate the image update factor.

14. The non-transitory computer readable medium of claim 10, wherein the steps of generating a motion corrected data model, generating an image update factor, and updating the image estimate are iteratively repeated for each of the plurality of gates in the at least one view.

15. The non-transitory computer readable medium of claim 10, wherein the motion corrected data model is generated by an intra-reconstruction motion correction method.

16. A system, comprising:

a first imaging modality;

a second imaging modality; and a computer in data communication with the first imaging modality and the second imaging modality, the computer configured to process data for medical imaging by:

receiving a set of first modality data including at least one view from the first imaging modality;

receiving a set of second modality data including the at least one view from the second imaging modality;

generating an image estimate of each of at least one view;

generating a motion corrected data model of the at least one view by forward projecting the image estimate using a motion estimate;

calculating an image update factor by comparing at least one of the plurality of gates to the motion corrected data model, wherein calculating the image update factor comprises comparing each of the plurality of gates to the motion corrected data model to generate a plurality of projection update factors, and wherein comparing each of the plurality of gates to the motion corrected data model comprises applying a merit function between the motion corrected data model and each of the plurality of gates to generate the plurality of projection update factors; and updating the image estimate by the image update factor.

17. The system of claim 16, wherein the first modality is a SPECT modality and the second modality is a CT modality.

18. A method of processing data for medical imaging, the method comprising:

providing a set of first modality data including at least one view comprising a plurality of gates;

providing a set of second modality data;

generating an image estimate for the at least one view from the set of first modality data;

generating a motion corrected data model of the at least one view by forward projecting the at least one view using a motion estimate;

generating an image update factor for the at least one of view by comparing at least one of the plurality of gates to the motion corrected data model, wherein generating the image update factor comprises:

comparing a set of first gate data to the motion corrected data model to generate a first image update factor, wherein comparing the set of first gate data to the motion corrected data model comprises applying a merit function between the motion corrected data model and the set of first gate data to generate a first projection update factor, and back projecting the first projection update factor to an image space to generate the first image update factor;

updating the image estimate by the first image update factor;

comparing a set of second gate data to the motion corrected data model to generate a second image updated factor; and     updating the image estimate by the second image update factor; and updating the image estimate by the image update factor.

19. A non-transitory computer readable medium storing computer executable instructions which cause a computer to execute the steps of:

generating a set of first modality data including at least one view, wherein the set of first modality data is generated by a first modality of an imaging system;

generating a set of second modality data including the at least one view, wherein the set of second modality data is generated by a second modality of the imaging system;

generating an image estimate of each of the at least one view;

generating a motion corrected data model of the at least one view by forward projecting the image estimate using a motion estimate;

calculating an image update factor by comparing at least one of the plurality of gates to the motion corrected data model, wherein calculating the image update factor comprises comparing each of the plurality of gates to the motion corrected data model to generate a plurality of projection update factors, and wherein calculating the image update factor further comprises back projecting each of the plurality of projection update factors into an image space to generate a plurality of gated image update factors and combining the plurality of gated image update factors to generate the image update factor; and     updating the image estimate by the image update factor.

\* \* \* \* \*

UNITED STATES PATENT AND TRADEMARK OFFICE
CERTIFICATE OF CORRECTION

| | |
|---|---|
| PATENT NO. | : 10,303,849 B2 |
| APPLICATION NO. | : 15/314481 |
| DATED | : May 28, 2019 |
| INVENTOR(S) | : Cachovan et al. |

Page 1 of 1

It is certified that error appears in the above-identified patent and that said Letters Patent is hereby corrected as shown below:

In the Specification

Column 2 Line 4 should read:
"generated for the at least one view from the set"

Column 2 Lines 7-8 should read:
"An image update factor is generated for the at least one view by comparing..."

Column 7 Lines 36-37 should read:
"After updating the image estimate 264 for each gate in the current view, the image updater module..."

Column 7 Lines 55-58 should read:
"comparing a projection of the current gate data and the motion-corrected data model to generate a difference image. The difference image may be determined by any suitable comparison..."

Column 9 Lines 7-8 should read:
"to further correct the data model/image estimate."

In the Claims

Column 13 Line 7 Claim 18 should read:
"generating an image update factor for the at least one view by comparing..."

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*